United States Patent [19]
Brugger

[11] Patent Number: 4,949,715
[45] Date of Patent: Aug. 21, 1990

[54] TRANSPORTABLE INHALATION DEVICE

[76] Inventor: Stephan Brugger, Etztalstrasse 21, 8137 Berg, Fed. Rep. of Germany

[21] Appl. No.: 231,812

[22] Filed: Aug. 12, 1988

[30] Foreign Application Priority Data

Aug. 12, 1987 [EP] European Pat. Off. ........ 87111686.9

[51] Int. Cl.$^5$ ............................................. A61M 16/00
[52] U.S. Cl. .......................... 128/204.21; 128/200.14
[58] Field of Search ...................... 128/204.18, 204.21, 128/203.13, 200.18, 204.23, 200.14; 417/38; 604/67, 123

[56] References Cited

U.S. PATENT DOCUMENTS

| | | | |
|---|---|---|---|
| 3,301,255 | 1/1967 | Thompson | 128/200.18 |
| 3,379,194 | 4/1968 | Ziermann | 128/200.18 |
| 3,613,677 | 10/1971 | Blasko | 128/204.21 |
| 3,705,689 | 12/1972 | Lee | 239/337 |
| 4,197,842 | 4/1980 | Anderson | 128/204.18 |
| 4,212,591 | 7/1980 | Lamontagne et al. | 417/38 |
| 4,244,361 | 1/1981 | Neubert | 128/204.21 |
| 4,257,415 | 3/1981 | Rubin | 128/204.21 |
| 4,301,793 | 11/1981 | Thompson | 128/204.21 |
| 4,328,796 | 5/1982 | Häkkinen | 128/203.13 |
| 4,396,015 | 8/1983 | Johnson | 128/200.14 |
| 4,443,218 | 4/1984 | De Cant, Jr. et al. | 604/67 |
| 4,807,616 | 2/1989 | Adahan | 128/204.21 |
| 4,823,787 | 4/1989 | Adahan | 128/203.27 |

Primary Examiner—Edgar S. Burr
Assistant Examiner—Aaron J. Lewis
Attorney, Agent, or Firm—Sughrue, Mion, Zinn, Macpeak & Seas

[57] ABSTRACT

The invention relates to a transportable inhalation device, which can be driven with an accumulator (25), independently of the electric network. In an aerosol mister (7) that is separated from the rest of the device, a medication solution is atomized by means of compressed-air, introduced to an aerosol. The compressed-air that is required for this is generated by a compressed-air generator 23. A hand-actuated valve (14), mounted on the aerosol mister (7), blocks the supply of compressed-air. The compressed air generator (23) is driven by an electric motor (24). The electric motor (23) is controlled by means of an electronic controller (31), to which a pressure sensor (30), which is arranged between the compressed-air generator (23) and the valve (14) is attached electrically. In response to this pressure sensor (30), the controller (31) automatically switches on the electric motor (24), as soon as a predetermined minimum pressure is exceeded within the compressed-air hose (11). Thus the compressed-air generator (23) is always driven only when by actuating the valve (14) the patient lets the compressed-air flow into the aerosol mister (7). The automatically, pressure-controlled operating method completely utilizes the electric energy stored in the accumulator (25), and permits the inhalation device of the invention to be operated in an especially efficient manner.

14 Claims, 2 Drawing Sheets

TRANSPORTABLE INHALATION DEVICE

The invention relates to a transportable inhalation device for the treatment of affected respiratory passages, having a housing, a compressed-air generator, an electric motor that drives the compressed-air generator, a power supply having at least one accumulator, an aerosol mister that is separated from the housing, and having a flexible compressed-air hose whose one end is connected to the compressed-air generator and whose other end is attached to the aerosol mister.

Such a portable inhalation device is already known from U.S. Pat. No. 4,257,415. The built-in accumulator permits inhalation treatments, independently of Prior to treatment, the aerosol mister must be filled with the medication solution; by means of the compressed-air, supplied by the compressed-air generator, this medication solution is atomized into a fine aerosol mist, which the patient inhales for treatment of the respiratory passages. In the known device the compressed-air generator or the electric motor, driving said generator, is turned on or off by means of a switch on the exterior of the housing.

The generator of compressed-air requires relatively much energy, which must be fed to the driving electric motor. In particular with portable device that are independent of the electric network, it is especially important to be as economical as possible with the electric energy, stored in the accumulator. Namely an efficacious respiratory-therapeutic treatment by means of inhalation of medication-containing aerosol takes approximately 15 min. An uninterrupted operation of the compressed-air generator for this period of time would result in the fact that only very few inhalation treatments could be performed until the capacity of the built-in accumulator was exhausted. Thus one endeavors to let the electric motor of the compressed-air generator run only when it is absolutely necessary for aerosol generatioon, thus during inhalation; during the subsequent exhalation process, the generation of compressed-air can be interrupted. It is impractical to continuously actuate the on- and off-switch, as mounted on the housing of the prior art inhalation device. Instead, the patient tends, for the sake of convenience, to remove only the aerosol mister from his mouth while exhaling and to let the device simply run so that approximately half of the time the aerosol is blown into the environment unprofitably. The result is not only a waste of valuable medication and undesired contamination of the surrounding air but also a premature exhaustion of the battery reserves.

Thus the object of the present invention is to provide a transportable inhalation device that permits with the pre-determined capacity of the built-in accumulator as long a treatment duration as possible and is characterized by its conventient operation.

The problem is solved by starting with a transportable inhalation device for treatment of affected respiratory passages of the aforementioned type. According to the first patent claim, the problem is solved by a manual valve, which is mounted on the aerosol mister and which blocks the supply of compressed-air, by a controller for controlling the electric motor, and by a pressure sensor that is arranged between the compressed-air generator and the valve, that monitors the pressure in the compressed-air hose, and that is electrically connected to the controller.

At the start of the inhalation treatment, the aerosol mister is connected to the compressed-air generator in the housing by means of the flexible compressed-air hose and the device is switched on. The pressure sensor arranged behind the compressed-air generator reports too little pressure within the hose so that the controller automatically lets the electric motor run until the compressed-air generator has built up at least the operating pressure required for aerosol misting. During this process, the valve mounted on the aerosol mister is closed so that no compressed air can escape. Controlled by the pressure sensor and the following controller, the electric motor turns off again after a short period of time. The device is ready to operate. —For the inhalation treatment itself, the patient takes the aerosol mister in his hand and puts its blow-out opening in his mouth. In actuating the valve which is placed in such a manner that it is convenient to handle, the ready-to-use compressed-air flows immediately into the aerosol mister in which it and the medication solution are atomized into the desired aerosol. The pressure drop within the compressed-air hose, resulting from the escape of the compressed-air into the aerosol mister is detected by the pressure sensor, whereupon the controller turns on the electric motor of the compressed-air generator, so that the pressure drop is compensated for as quickly as possible. As long as the patient inhales, the valve on the aerosol mister remains open so that constant compressed-air is supplied by the compressed-air generator via the compressed-air hose. If the patient then exhales into the open environment, the supply of compressed-air into the aerosol mister is blocked by the manually actuated valve. The result is an almost sudden increase in pressure within the compressed-air hose. Upon reaching the pre-determined maximum pressure, the electric motor in the device is immediately turned off, and in particular until the pressure sensor registers again a pressure drop due to the opening of the valve on the aerosol mister.

The automatic on and off switching of the electric motor in rhythm with the inhalation and exhalation process, triggered by the actuation of the valve on the aerosol mister, has the advantage that the compressed-air generator only compresses the air when said air is actually required to generate the aerosol. The generation of compressed-air can be interrupted at any time by the patient by the simple and convenient manner of actuating the valve on the aerosol mister. Thus it is not longer necessary to set up the inhalation device in a convenient to handle manner. With a normal time ratio of approximately 1:1 for inspiration and expiration, the inhalation device, configured according to the invention, permits at least twice as many inhalations to be performed due to the intermittent drive of the compressed-air generator, than would be possible with a comparable device with pressure monitored control of the electric motor drive.

In a preferred embodiment of the inhalation device in accordance with the invention, the pressure sensor is mounted within the housing. All electrical components and the associated connections and the connecting cables, which are generally susceptible to moisture and dirt, are, therefore, within the protective housing. The parts that make contact with the medication solution or aerosol, such as aerosol mister, valve, pressure hose function purely mechanically. Thanks to this logical separation of electrical and mechanical components, the inhalation device of the invention is characterized by its ruggedness and especially low susceptibility to interference.

It is expedient for the controller of the device to contain a two-point regulator so that if the pressure in the compressed-air hose drops below a bottom limiting value, the electric motor of the compressed-air generator is turned on and upon reaching an upper limiting value for the pressure, the electric motor is turned off again. Such a pressure control between an upper and a bottom limiting value can be actualized in a simple manner by means of switching technology and operates reliably in the field.

It has been proven to be expedient to switch the electric motor on when the pressure within the pressure hose falls below 0.7 bar and to switch it off again at a pressure of more than 1 bar. Since at least 1 bar of pressure occurs when the valve on the aerosol mister is closed, the aerosol mister begins to operate without time delay in a direct response to actuating the valve. The selected pressure difference of 0.3 bar between the upper and lower limiting value for the pressure prevents an extremely sensitive responsivity of the controller to pressure fluctuations.

Preferably a d.c. electric motor is used as the electric motor. Usually membrane compressors, constructed especially for such inhalation devices, are used as compressed-air generators.

In an advantageous embodiment of the inhalation device of the invention, the pressure sensor is a piezo element, whose output voltage can be processed directly by an electronic controller for the electric motor.

The operating comfort is further increased if the valve on the aerosol mister is actuated by pressure on a push button. Preferred is an embodiment in which the valve opens when the push button is pressed so that the compressed-air flows from the compressed-air hose into the aerosol mister, and upon releasing the push button automatically closes. Thus it is assured that when the aerosol mister is put away, the device always turns off automatically and immediately.

In another embodiment of the invention, the compressed-air hose is connected to the compressed-air generator via a receptacle mounted on the outside of the housing. For the purpose of cleaning and for transport, the compressed-air hose and the aerosol mister attached thereto can be separated quickly and simply from the rest of the device.

Despite the design of the drive control of the compressed-air generator of the invention, the built-in accumulator will be exhausted after carrying out a few inhalation treatments. In an especially practical further development of the invention, the built-in power supply includes for this reason a recharger for the accumulator and a power pack. The operating readiness can be reproduced without having to take along a separate power pack. An additional advantage is yielded by the possibility of being able to charge the inhalation device also directly from the electric network despite empty accumulator.

Instead of the switch that is on conventional devices for turning directly on and off the electric motor drive of the compressed-air generator, the inhalation device of the invention has an on-switch for activating the electronic control that is preferably on the outside of the housing. The interruption of the voltage supply that is made possible by this prevents unintentional no-load operation of the device, for example if the aerosol mister is by accident attached in such a manner that it is not pressure sealed or the compressed-air hose is damaged.

An embodiment of the invention is explained in detail with the aid of the attached drawings as follows.

Figure 1:
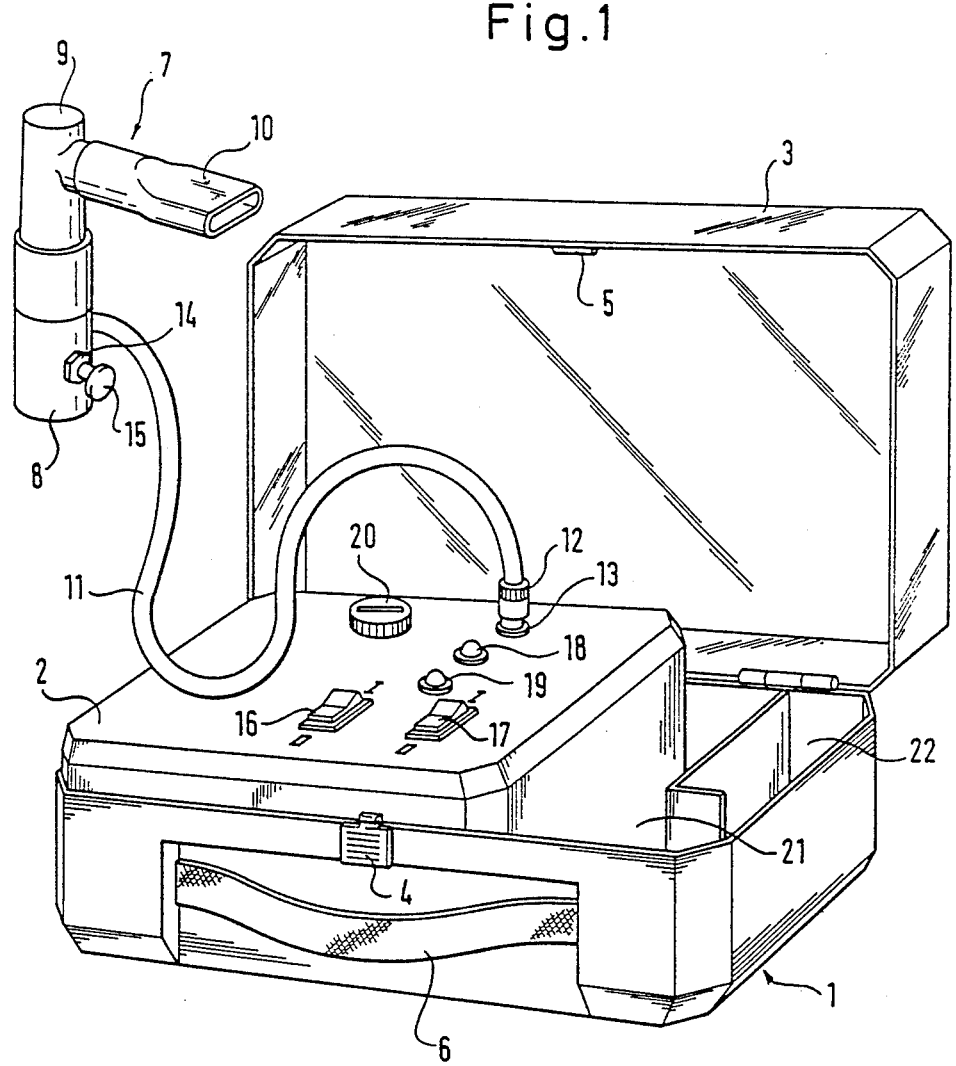
FIG. 1 is a perspective view of a transportable inhalation device.

The transportable inhalation device, shown in FIG. 1, has a housing 1, made of plastic, in which all of the electrical components are housed. On its upper side the housing 1 has a level cover plate 2. On the back side of the housing 1, a snap cover 3 of the transparent plastic is arranged to swivel and overlaps the cover plate 2 in closed state. A snap lock 4 prevents the closed snap cover 3 in the interaction with a small projection 5 from popping open. A handle 6 is attached to the front of the housing 1.

The inhalation device includes an aerosol mister 7, which the patient takes into his hand. Said mister comprises a lower part 8, which contains the medication solution to be misted, an upper part 9 and a mouth piece 10. A compressed-air hose 11 serves to supply compressed air into the cavity of the aerosol mister 7. The free end of the compressed-air hose 11 terminates in a coupling 12, which is inserted into a receptacle 13, mounted on the cover plate 2 of the housing 1. Furthermore, a valve 14, which blocks the supply of compressed-air into the cavity of the aerosol mister 7, is in the lowre part 8 of the aerosol mister 7. When the push button 15 that is under pre-tension of a spring, is pressed, the valve 14 opens; and when said button is released, the valve automatically closes again immediately.

A power switch 16, a switch 17 and an accumulator status light 18, and a recharger status light 19, are mounted on the cover plate 2 of the housing 1. The screw lock of a replaceable air filter is designated with the number 20. A compartment 21, which is open towards the top, serves to receive the aerosol mister 7 during transport of the inhalation device. Another compartment 22 is also provided for accessories.

Figure 2:
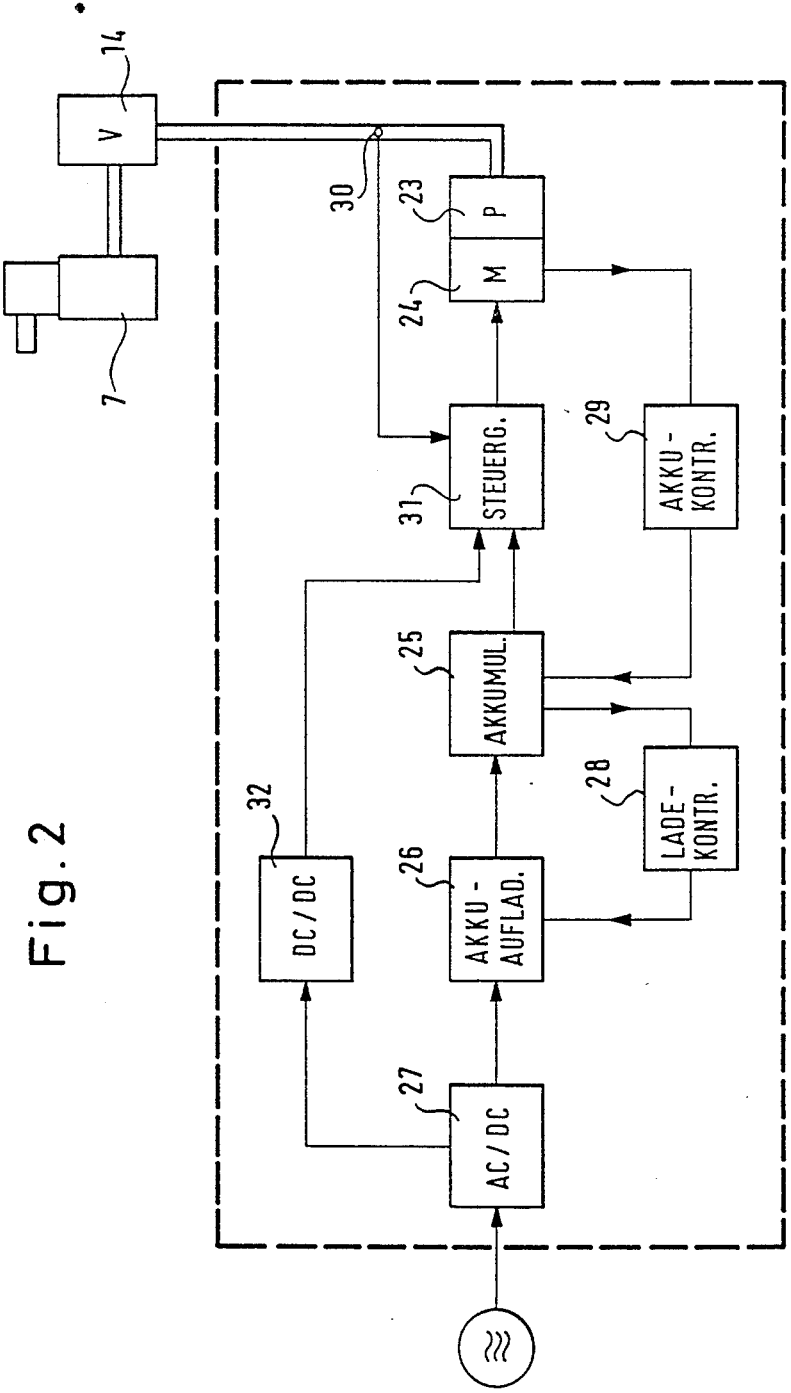
FIG. 2 is a simplified block circuit diagram of the inhalation device of FIG. 1.

In the block circuit diagram of FIG. 2, the electrical and mechanical components of the inhalation device are shown schematically. The nucleus is a compressed-air generator 23, which is designated, for example, as a membrane compressor. A flanged d.c. electric motor 24 serves as the drive unit. The power supply includes a rechargeable accumulator 25, a recharger 26, and a power pack 27 for converting the alternating electric voltage into the requisite d.c. voltage. A charging control 28 monitors the charging of the accumulator 25. The charging process is indicated by the light emitted by the charge status light 19 on the cover plate 2 of the housing 1. An accumulator control 29, which permits the accumulator status light 18 to light up when a specific minimum voltage has been exceeded, serves to monitor the charge state of the accumulator 25 (cf. FIG. 1).

The pressure chamber of the compressed-air generator 13 is connected to the aerosol mister 7 via the inserted compressed-air hose 11, whereby the valve 14 blocks the supply of compressed-air. A pressure sensor 30, which is designed as a piezo element, is arranged between the compressed-air generator 23 and the hand-actuated valve 14. This pressure sensor 30 is electrically connected to an electronic controller 31, which drives the electric motor 24. When operating independently of the electric network, the electronic controller 31 obtains the operating current for the electric motor 24, supplied by the accumulator 25. If current is available, the power is supplied via the power pack 27 and an intermediate d.c. converter 32.

After the switch 17 has been turned on, the electric motor 24 drives—controlled by the electric controller 31—the compressed-air generator 23 until an internal pressure of approximately 1 bar prevails in it on the end of the compressed-air hose 11, tightly closed by the valve 14. In response to the pressure sensor 30, the controller 31, which contains a two-point regulator, switches off the electric motor 24. If the patient then opens the valve 14 by actuating its push button 15 (cf. FIG. 1), the compressed-air flows out of the compressed-air hose 11 into the aerosol mister 7. The aerosol mister starts momentarily; the generated medication mist can be inhaled by the patient through the mouth piece 10. After the compressed-air escapes into the aerosol mister 7, the pressure in the compressed-air hose 11 drops. Upon reaching the anticipated minimum pressure of about 0.7 bar, the controller 31 switches on again the electric motor 24 in response to the pressure sensor 30 so that the compressed-air generator 23 pumps compressed air again into the compressed-air hose 11. In this manner, the drive pressure, required for aerosol misting, is maintained.

If the patient releases the push button 15 of the valve 14, the compressed-air supply—and thus the aerosol generation—is momentarily interrupted. In the compressed-air hose 11, which is now closed with a pressure seal, the pressure increases almost suddenly. Upon reaching the preset maximum pressure of about 1 bar, the controller 31 turns off the electric motor 24. The compressed-air generator 23 will not be driven again until the patient inhales again and then the valve 14 reopens by renewed force on the push button 15. As long as the inhalation device is switched on, a constant pressure between 0.7 bar and 1 bar is maintained within the compressed-air hose 11, regardless of whether the valve 14 is opened or not. The automatic control of the electric motor 24 by means of pressure sensor 30 and the controller 31 provides that the compressed-air generator 23 operates only if aerosol is generated.

I claim:

1. Transportable inhalation device for treatment of affected respiratory passages, comprising:
   a compressed-air generator,
   an electric motor, which drives the compressed-air generator;
   a power supply for the motor with at least one accumulator;
   an aerosol mister for supplying gasses to the affected respiratory passages;
   a flexible compressed-air hose having an inlet and an outlet, the inlet being connected to the compressed-air generator and the outlet being connected to the aerosol mister;
   a hand-actuated valve, which is mounted on the aerosol mister and which blocks the supply of compressed air when actuated;
   a controller for controlling the electric motor; and
   a pressure sensor in said housing which monitors the pressure in the compressed-air hose between the compressed-air generator and the valve and transmits an indication of the monitored pressure to the controller for controlling the motor in response to the pressure indication;
   where said controller comprises a two-point regulator so that when the pressure in the compressed-air hose drops below a lower limiting value, the electric motor of the compressed-air generator is switched on and when the pressure reaches an upper limiting value, the compressor is switched off.

2. Inhalation device, as claimed in claim 1, wherein the electric motor is switched on at a pressure of below 0.7 bar.

3. Inhalation device, as claimed in claim 2 wherein the electric motor is swtiched off at a pressure of more than 1 bar.

4. Inhalation device, as claimed in claim 2, wherein the electric motor is a d.c. motor.

5. Inhalation device, as claimed in claim 1, wherein the compressed-air generator a membrane compressor.

6. Inhalation device, as claimed in claim 1, wherein the pressure sensor is a piezo element.

7. Inhalation device, as claimed in claim 7, wherein the valve on the aerosol mister is actuated by pressing on a push button, the push button being easily reached by a person's hand when the hand is holding the mister.

8. Inhalation device, as claimed in claim 7, wherein the valve opens when the push button is pushed so that compressed air from the compressed-air hose flows into the aerosol mister and automatically closes again when the push button is released.

9. Inhalation device, as claimed in claim 1, wherein the compressed-air hose is connected to the compressed-air generator via a receptacle, mounted on the outside of the housing.

10. Inhalation device, as claimed in claim 1, wherein the power supply comprises a charger for charging the accumulator.

11. Inhalation device, as claimed in claim 1, wherein a switch for actuating the controller is provided on the outside of the housing.

12. Inhalation device as claimed in claim 1 further comprising a portable housing for containing the compressed air generator, the electric motor and the accumulator.

13. Inhalation device as claimed in claim 12, wherein the housing further contains the controller and the pressure sensor.

14. Inhalation device as claimed in claim 10, wherein the charger accepts direct current and comprising a converter for converting supplied alternating current to a direct current

* * * * *